(12) United States Patent  
Guillette

(10) Patent No.: US 8,651,102 B2
(45) Date of Patent: Feb. 18, 2014

(54) EMERGENCY VENTILATION APPARATUS, SYSTEM, AND METHOD

(76) Inventor: Donald F. Guillette, Auburndale, FL (US)

( * ) Notice: Subject to any disclaimer, the term of this patent is extended or adjusted under 35 U.S.C. 154(b) by 775 days.

(21) Appl. No.: 12/360,616

(22) Filed: Jan. 27, 2009

(65) Prior Publication Data
US 2009/0188509 A1 Jul. 30, 2009

Related U.S. Application Data

(60) Provisional application No. 61/023,942, filed on Jan. 28, 2008.

(51) Int. Cl.
A61M 16/00 (2006.01)
A61M 15/00 (2006.01)
A62B 7/00 (2006.01)
A62B 9/00 (2006.01)
A62B 18/00 (2006.01)
A62B 9/06 (2006.01)

(52) U.S. Cl.
USPC ............. 128/200.26; 128/200.24; 128/207.17

(58) Field of Classification Search
USPC .................. 128/202.21, 207.17, 200.26, 198, 128/202.27; 600/193; 604/174
See application file for complete search history.

(56) References Cited

U.S. PATENT DOCUMENTS

| | | | |
|---|---|---|---|
| 3,520,071 A | 7/1970 | Abrahamson et al. | |
| 3,662,076 A | 5/1972 | Gordon et al. | |
| 4,091,816 A * | 5/1978 | Elam | 128/207.15 |
| 4,266,540 A | 5/1981 | Panzik et al. | |
| 4,270,529 A * | 6/1981 | Muto | 128/200.26 |
| 4,530,354 A * | 7/1985 | Froilan | 128/207.17 |
| 4,559,939 A | 12/1985 | Levine et al. | |
| 5,026,352 A * | 6/1991 | Anderson | 604/178 |
| 5,033,134 A | 7/1991 | Burchett | |
| 5,069,206 A * | 12/1991 | Crosbie | 128/207.17 |
| 5,233,978 A | 8/1993 | Callaway | |
| 5,423,685 A | 6/1995 | Adamson et al. | |
| 5,446,932 A | 9/1995 | Voorhis | |
| 5,509,810 A | 4/1996 | Schertz et al. | |
| 5,513,633 A * | 5/1996 | Islava | 128/207.17 |
| 5,522,102 A | 6/1996 | Vayda | |
| 5,806,516 A * | 9/1998 | Beattie | 128/207.17 |
| 5,941,710 A | 8/1999 | Lampotang et al. | |
| 6,105,573 A * | 8/2000 | Delaplane et al. | 128/200.26 |
| 6,196,220 B1 | 3/2001 | Idris | |
| 6,425,394 B1 | 7/2002 | Weinstein et al. | |
| 6,500,009 B1 | 12/2002 | Brault et al. | |

(Continued)

Primary Examiner — Lynne Anderson
Assistant Examiner — Bradely Philips
(74) Attorney, Agent, or Firm — Allen, Dyer, Doppelt, Milbrath & Gilchrist, P.A.

(57) ABSTRACT

An emergency ventilation apparatus, system, and method for providing ventilation to patients in emergency situations, the system comprising an angled laryngoscope handle and a ventilation-aid securement device. The handle is configured to hold a laryngoscope blade between approximately twenty and forty degrees relative to a lower portion of the handle for more effective intubation of patients. The securement device fits atop a portion of a ventilating mask and is adjustably secured to the patient fitted with the mask by an adjustable strap or similar device. The securement device fits flexibly over the mask providing a seal between the mask and the patient's face. A version of the securement device includes a thumbscrew for engaging with the mask to secure it. Another version of the securement device is further capable of securing an endotracheal tube to a patient using a thumbscrew to advance a retaining arm for engaging the tube.

8 Claims, 5 Drawing Sheets

(56) References Cited

U.S. PATENT DOCUMENTS

| | | |
|---|---|---|
| 7,316,568 B2 | 1/2008 | Gordon et al. |
| 7,748,384 B2 * | 7/2010 | Ho et al. .................. 128/207.11 |
| 2003/0024530 A1 | 2/2003 | Sniadach |
| 2005/0244801 A1 | 11/2005 | DeSalvo |
| 2006/0081248 A1 | 4/2006 | McDonald |
| 2006/0121430 A1 | 6/2006 | Winnike et al. |
| 2007/0054254 A1 | 3/2007 | Cook et al. |
| 2007/0221226 A1 | 9/2007 | Hansen et al. |
| 2007/0240720 A1 | 10/2007 | Castro |
| 2007/0272251 A1 * | 11/2007 | Hodge .................... 128/207.17 |
| 2008/0295849 A1 * | 12/2008 | Reynolds et al. ............. 128/859 |

* cited by examiner

EMERGENCY VENTILATION APPARATUS, SYSTEM, AND METHOD

CROSS-REFERENCE TO RELATED APPLICATION

This application claims priority to provisional application 61/023,942, filed Jan. 28, 2008, entitled Emergency Ventilation and Training Device, System, and Associated Methods.

BACKGROUND

The present invention relates to emergency devices and methods for ventilating patients, particularly to laryngoscope handles and devices for securing a mask or endotracheal tube to a patient to provide ventilation.

Note that herein all references made to "oxygen" are to be understood to include "air" as well.

Conventional masks used to supply oxygen to a patient are fitted over the nose and mouth of the patient and typically use one or more elastic bands placed behind the patient's ears or around the head to secure the mask to the patient's face. Oxygen is fed into the mask through a tube.

One commonly-used type of ventilation device utilizing a mask is a bag-valve-mask, also called a BVM. The bag-valve-mask is a hand-held device used to provide ventilation to a patient who is not breathing or who is breathing inadequately. The bag-valve-mask is a normal part of a resuscitation kit for trained professionals, such as ambulance crews. The bag-valve-mask is also frequently used in hospitals and is an essential part of a crash cart.

The bag-valve-mask consists of a flexible air chamber attached to a mask via a shutter valve. When the air chamber or "bag" is squeezed, the device forces air through the mask and into the patient's lungs. When the bag is released it self-inflates, drawing in either ambient air or a low pressure oxygen flow supplied from a regulated cylinder. In response, the patient's lungs deflate through the one way valve.

A bag-valve-mask without the mask is called a bag-and-valve combination. The bag-and-valve combination, absent the mask, can be attached to an alternate airway adjunct, such as an endotracheal tube. In this way, an endotracheal tube can be used in place of a mask, as discussed below.

When ventilating a patient using a mask, the mask is positioned and secured over the patient's nose and mouth to obtain a good seal so as to ensure oxygen does not escape from around the mask. One common method for obtaining a seal is called a "CE" clamp formation. The CE clamp formation involves using the index finger and thumb on the mask, forming a "C," and remaining on the jaw line, forming an "E," to secure the mask to the patient. A proper CE clamp can be even more difficult to maintain if the caregiver with smaller hands is required to provide adequate oxygen flow or tidal volume through the use of a bag-valve-mask or similar device. Other factors can also interfere with providing an effective seal around a mask, such as the position of accident victims, as when in an upright seated position.

During surgery, and in emergency situations, it may become necessary to intubate a patient. This is particularly true in emergency situations where a patient's mouth, throat, or tracheal passage becomes blocked by blood, mucus, or other obstruction. Intubation is the process of inserting an endotracheal tube into the trachea of the patient to provide a clear airway to the patient's lungs. Oxygen is then supplied through the tube. Intubation usually requires general anesthesia and muscle relaxation, but can be achieved in a conscious patient with anesthesia. In an emergency situation, intubation can be performed without anesthesia, although this is uncomfortable for the patient. Intubation is usually performed by first visualizing the larynx using a handheld laryngoscope.

The laryngoscope is typically comprised of two parts, a handle and a removable blade. The handle is typically made of metal and in the approximate shape of an elongated cylinder with a hollow chamber for holding batteries to power a light commonly found on the blade. The removable blade is elongated and generally made of metal. The two main types of blades used in a laryngoscope are curved blades and straight blades. A base of the blade attaches to a top of the handle, with the base of the blade aligned basically perpendicular to the handle.

To begin intubation, a blade is selected and connected to the laryngoscope handle. The handle and blade are then used to visualize the larynx so that the patient can be intubated. The caregiver first opens the patient's mouth and inserts a tip of the blade into the mouth and slides the blade to the base of the tongue. Given the angle of the blade to the handle, the handle will be transverse to the mouth as the blade is inserted. This partially obscures the caregiver's view of the mouth, which sometimes results in the caregiver striking and damaging the patient's teeth or lip with the blade. To bring the larynx into view, the patient's chin is lifted upwards and forward at the same time. The blade is then properly located in the patient's mouth with the precise location dependent upon the type of blade used. With the blade properly positioned, the caregiver can now apply a degree of force to the handle to lift the patient's upper jaw. The handle is raised upwardly and away from the patient to an angle of approximately forty-five degrees relative to the patient's mandible. At this point, the larynx should come into view.

A common technique used by caregivers in raising upwardly on the handle is to grip the handle near the blade so as to have more control over the blade and then twisting the wrist to pull the handle upwardly. Again, the shape of the handle can obscure the caregiver's view of the trachea as the handle is transverse to the mouth. Sometimes this twisting of the wrist can lead to a tendency to use the teeth as a fulcrum for the laryngoscope, which can cause damage to the teeth.

Once the larynx is in view, the endotracheal tube is placed through the mouth and down into the trachea between the vocal folds. An end of the endotracheal tube is equipped with an inflatable cuff. When a top end of the cuff clears the vocal folds, insertion of the endotracheal tube is halted and the cuff is inflated. The cuff provides a seal to prevent aspiration and leakage of oxygen. The laryngoscope is removed, and the opposite end of the endotracheal tube is attached to an oxygen source, such as a bag-and-valve combination.

It is now important that the endotracheal tube be secured in a stable position, likely for an extended period of time. Unintended movement of the endotracheal tube can harm delicate tissues in the patient's trachea. It is also important, especially in emergency situations, that the caregiver's hands remain free to perform other treatment.

Typically, tape is wrapped around the endotracheal tube and also attached to the facial area around the mouth to secure the endotracheal tube in place. Unfortunately, if the taping is done incorrectly the tube can move about in the patient's mouth and irritate the trachea. In addition, the very flexibility of the adhesive tape itself can permit some lateral movement of the endotracheal tube. Another concern is that saliva can collect on the tape and cause the tape to lose adhesion, requiring it to be reapplied. Such periodic reapplication can irritate the patient's skin. Making adjustments to the endotracheal tube also generally requires removal and reapplication of the tape. Removing the tape, however, cannot ordinarily be done rapidly, as might be necessary in an emergency situation. The tape also hinders access to the mouth area for such care as suctioning out the mouth.

As an alternative to tape, a tube-holding device can be used to secure the endotracheal tube in position. Many such devices exist in the prior art. Typically, after the endotracheal tube has been inserted through a patient's mouth and down into the trachea, a tube-holding device having a generally central opening is lowered over the tube. The device is secured over the mouth using adhesive tape, one or more bands wrapped about the patient's head, or some other way of fastening. The tube is then secured in position within the device by such means as adhesive tape or a clamp surrounding the central opening of the device. Other means for securing the endotracheal tube are also possible. For example, one prior art device uses a thumbscrew to contact the tube and thereby secure it. Some tube-holding devices also incorporate a bite block secured to a face plate. The face plate generally covers a substantial portion of the face around the patient's mouth while the bite block is inserted into the mouth. A disadvantage of the bite block is that it can sometimes cause trauma to the interior of the mouth.

There is a need, therefore, for a device that secures a mask to a patient's face in a manner that ensures a good seal around the mask in emergency situations and that frees up the hands of a caregiver to attend to other treatment needs. There is also a need for a device to secure an endotracheal tube to a patient in a manner that prevents substantial movement of the tube once installed, that allows for easy repositioning of the installed tube, and that offers a minimum of skin irritation and mouth trauma. There is a further need for a laryngoscope handle that allows for better viewing of the inside of the mouth so as to effect an easier installation of an endotracheal tube without causing undue injury, as well as a handle that provides better leverage for lifting the jaw, thereby relieving a tendency to use the teeth as a fulcrum and thus causing damage.

SUMMARY OF THE INVENTION

In accordance with the present invention, a system for providing emergency ventilation to patients includes a ventilation-aid securement device and an angled laryngoscope handle. A ventilation-aid securement device is provided that ensures a good seal around a ventilating mask in emergency situations while at the same time securing the mask to a patient's face, thereby allowing a caregiver to attend to other treatment needs. The ventilation-aid securement device is also capable of securing an endotracheal tube to a patient in a manner that prevents substantial movement of the installed tube, that allows for easy repositioning of the installed tube, and that offers a minimum of skin irritation and mouth and throat trauma.

An angled laryngoscope handle is also provided that allows for better viewing of the inside of a patient's mouth and the trachea so as to effect easier installation of an endotracheal tube, helping avoid undue injury to the teeth and lip. The angled handle also provides better leverage for lifting the patient's jaw, thereby relieving a tendency of caregivers to use the teeth as a fulcrum and again causing damage.

The system for providing emergency ventilation to patients provides a ventilation-aid securement device and an angled laryngoscope handle to give healthcare professionals greater opportunity to provide effective care for patients while reducing the potential for causing undue injury as a result of intubation.

The ventilation-aid securement device fits atop a ventilating mask fitted to a patient's face. An adjustable securing device, such as an adjustable strap, is attached to the securement device at one end while the unattached end is fitted around the patient's head and then also attached to the securement device. The strap can be adjusted to apply more or less pressure on the securement device to hold the mask securely to the patient's face.

A flexible face plate of the securement device contacts a surface of the mask and bends downwardly as pressure is applied to the device by the adjustable strap. This flexibility allows the securement device to better conform to the surface of the mask, thereby better distributing the downward force to help hold the mask in place on the face. The configuration of the ventilation-aid securement device allows the device to adapt easily to different styles and shapes of masks.

A version of the ventilation-aid securement device is also capable of securing an endotracheal tube to a patient. Following intubation, the securement device is lowered over an end of the installed tube and placed against the patient's mouth and facial area adjacent to the mouth. A thumbscrew works with a retaining arm to secure the endotracheal tube in position. Again, an adjustable securing device, such as an adjustable strap, is attached to the securement device at one end while the unattached end is fitted around the patient's head and also attached to the securement device. The strap can then be adjusted as needed.

The angled laryngoscope handle is used to prepare a patient for intubation. The base of a laryngoscope blade is secured in an upper portion of the handle at an angle between approximately twenty and forty degrees relative to a lower portion of the handle. This is in contrast to typical prior art handles that are angled virtually perpendicular to the base of their installed blades. The angled handle allows for a better view of the mouth and the trachea than prior art laryngoscope handles. In addition, the handle provides greater leverage in lifting the jaw of a patient than prior art handles, due to the angle of the handle.

BRIEF DESCRIPTION OF DRAWINGS

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings, in which:

DESCRIPTION

Figure 1:
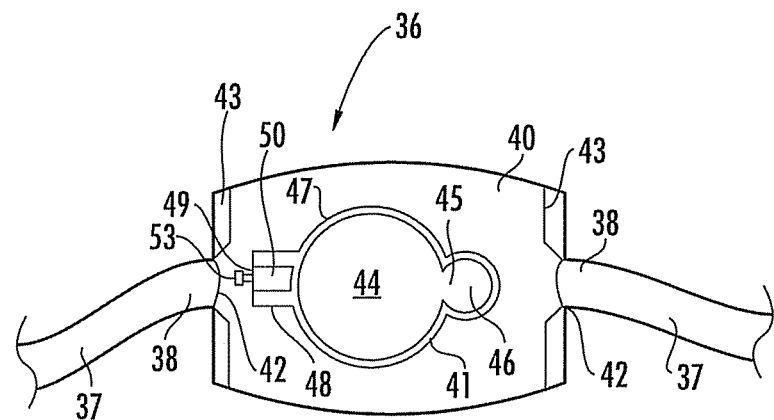
FIG. 1 is a top plan view of a ventilation-aid securement device absent a retaining arm, in accord with the present invention.

Note that herein all references made to "oxygen" are to be understood to include "air" as well.

Embodying the principles of the present invention is a system for providing emergency ventilation to patients comprising a ventilation-aid securement device and a laryngoscope handle. A preferred embodiment of the system is depicted in FIGS. 1-6 and designated generally by reference numeral 10.

Figure 2:
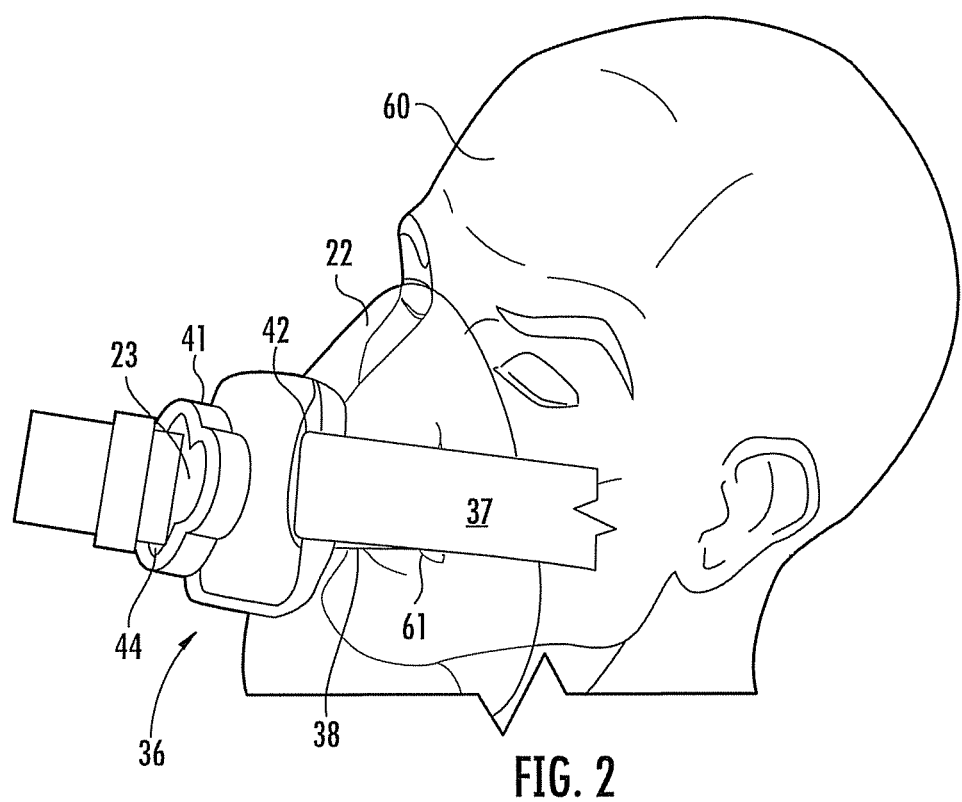
FIG. 2 is a left side perspective view of a patient fitted with a mask secured in place by the ventilation-aid securement device shown in FIG. 1.

Referring now to FIG. 1, the emergency ventilation system 10 includes a ventilation-aid securement device 36 for securing a ventilating device 14, 22 (see FIGS. 2, 5, and 6) to a patient 60 (see FIGS. 2, 3, 5, and 6), such as an endotracheal tube 14 (see FIGS. 5 and 6) or a ventilating mask 22 (see FIG. 2). In the present embodiment, the securement device 36 is envisioned to be made of flexible plastic. In alternate embodiments, however, other flexible materials might be used to construct a ventilation-aid securement device 36.

Continuing with FIG. 1, the securement device 36 includes an elongated face plate 40 that is generally rectangular and approximately one-half inch thick. The face plate 40 is dimensioned to cover the mouth 61 (see FIG. 2) and immediate surrounding facial area of a patient 60. The face plate 40 is flexible so as to conform to a curved surface, such as a surface of a ventilating mask 22 or the mouth 61 and surrounding facial area of the patient 60. The face plate 40 has opposing side portions 43, each containing a strap opening 42 for receiving an end portion 38, 39 (see FIGS. 2, 5, and 6) of a strap 37.

Referring now to FIG. 2, the securement device 36 also includes the adjustable strap 37. The strap 37 is placed around the head of the patient 60 and adjustably attached to the securement device 36. A first end portion 38 of the strap 37 is attached to a first strap opening 42 of the face plate 40. A second opposing unattached end portion 39 (see FIG. 5) of the strap 37 is equipped with Velcro® permitting the second end portion 39 to be passed through a second strap opening 42 and adjustably secured there. Note that in alternate embodiments, other fastening modes might be used for adjustably securing a strap 37 to a ventilation-aid securement device 36, such as buckles or hook-and-latch systems.

Referring now to FIG. 1, the ventilation-aid securement device 36 also includes a securement housing 41 that is generally oval-shaped and approximately centered atop the face plate 40. The securement housing 41 is formed integral with an upper surface of the face plate 40 and is used for receiving and securing a ventilating device 14, 22 (see FIGS. 2, 5, and 6). Although the securement housing 41 can receive and secure both the endotracheal tube 14 (see FIGS. 5 and 6) and the mask 22 (see FIG. 2), the securement housing 41 is used to secure only one ventilating device 14, 22 at a time.

Continuing with FIG. 1, the securement housing 41 includes a continuous wall 47 that defines two apertures: an oxygen-supply inlet aperture 44 and a tube aperture 46. The oxygen-supply inlet aperture 44 is in the general shape of a cylinder and sized for closely receiving an oxygen-supply inlet 23 (see FIG. 2) of the mask 22 (see FIG. 2). The tube aperture 46 is in the general shape of an ovate cylinder and of smaller diameter than the oxygen-supply inlet aperture 44. The tube aperture 46 is sized for closely receiving the endotracheal tube 14 (see FIGS. 5 and 6). In addition, the ovate shape of the tube aperture 46 allows for the tube to be wedged within the tube aperture 46 to further secure it in place. The oxygen-supply inlet aperture 44 is adjacent the tube aperture 46, with a narrow opening 45 connecting the two apertures 44, 46.

Still referring to FIG. 1, the securement housing 41 further includes a thumbscrew housing 48 located adjacent the oxygen-supply inlet aperture 44 in opposition to the tube aperture 46. The thumbscrew housing 48 has a threaded opening 49 for receiving a thumbscrew 53 therein. A threaded portion 54 of the thumbscrew 53 is of sufficient length to protrude through the thumbscrew housing 48 and into the adjacent oxygen-supply inlet aperture 44. After the oxygen-supply inlet aperture 44 has received the oxygen-supply inlet 23 of the mask 22, the thumbscrew 53 is advanced to make contact with the oxygen-supply inlet 23 to secure the mask 22 in place.

Figure 3:
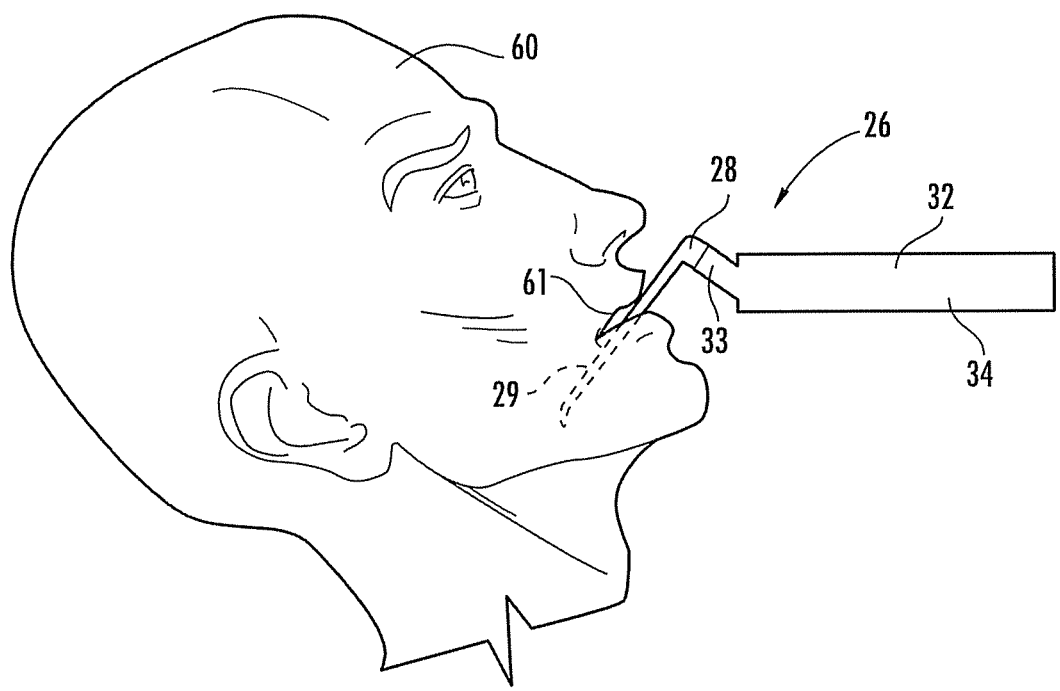
FIG. 3 is a right side elevational view of a patient being prepared for intubation using a laryngoscope handle, in accord with the present invention, fitted with a laryngoscope blade.

Referring now to FIG. 3, the emergency ventilation system 10 includes an angled laryngoscope handle 32. A base of a laryngoscope blade 28 is secured in an upper portion 33 of the handle 32, the handle 32 and blade 28 comprising a laryngoscope 26. The laryngoscope 26 is used to peer into the larynx of the patient 60 to aid in intubating. In the present embodiment, the laryngoscope handle 32 is envisioned to be made of metal. In alternate embodiments, however, other durable materials might be used to construct a laryngoscope handle 32.

Continuing with FIG. 3, a lower portion 34 of the laryngoscope handle 32 is elongated and substantially cylindrical with a cavity (not shown) for carrying batteries (not shown) to power a light 29 on the blade 28. A coupling (not shown) used to detachably fix the blade 28 to the upper portion 33 of the handle 32 also provides for transmitting power from the batteries to the light 29. Note that in alternate embodiments other methods might be used to power the light on the laryngoscope blade 28.

Still referring to FIG. 3, the blade 28 is secured to the upper portion 33 of the handle 32 such that a longitudinal axis extending along the base of the blade 28 intersects a longitudinal axis of the lower portion 34 of the handle 32 at an angle between approximately twenty and forty degrees. At this angle, the handle 32 permits the caregiver a better view of the mouth 61 and trachea of the patient 60 than laryngoscope handles that secure their blades at a substantially perpendicular angle. In addition, this angle provides the caregiver a good angle of leverage for lifting the jaw of the patient 60. Note that in alternate embodiments a laryngoscope handle 32 might be configured differently to achieve an angle of approximately twenty to forty degrees between blade 28 and handle 32.

Figure 5:
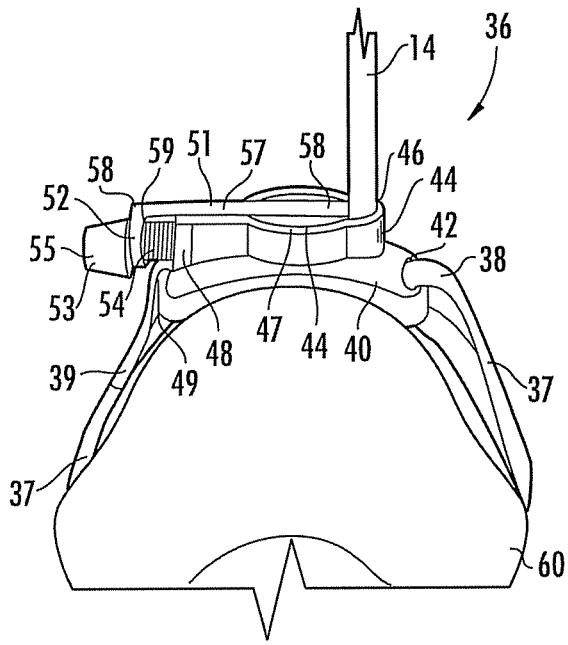
FIG. 5 is a bottom perspective view of the head of the patient shown in FIG. 3 now intubated with an endotracheal tube secured in place by the ventilation-aid securement device shown in FIG. 4.
Figure 6:
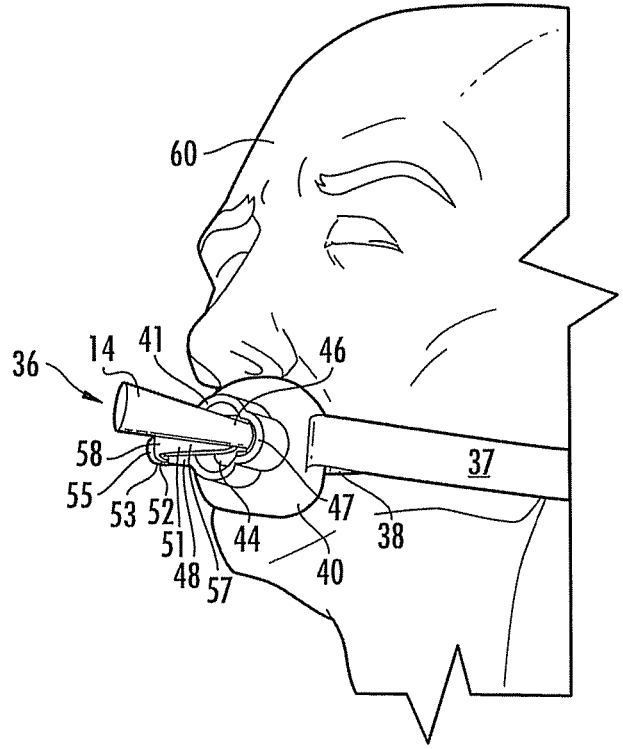
FIG. 6 is a left side perspective view of FIG. 5.

Referring now to FIGS. 5 and 6, after the laryngoscope handle 32 (see FIG. 3) and attached blade 28 (see FIG. 3) have been used to help the caregiver intubate the patient 60 with the endotracheal tube 14, the ventilation-aid securement device 36 is lowered over an end of the tube 14. The tube aperture 46 of the securement housing 41 receives the end of the endotracheal tube 14. The tube 14 is now in position to be secured in place using a retaining arm 51.

Figure 4:
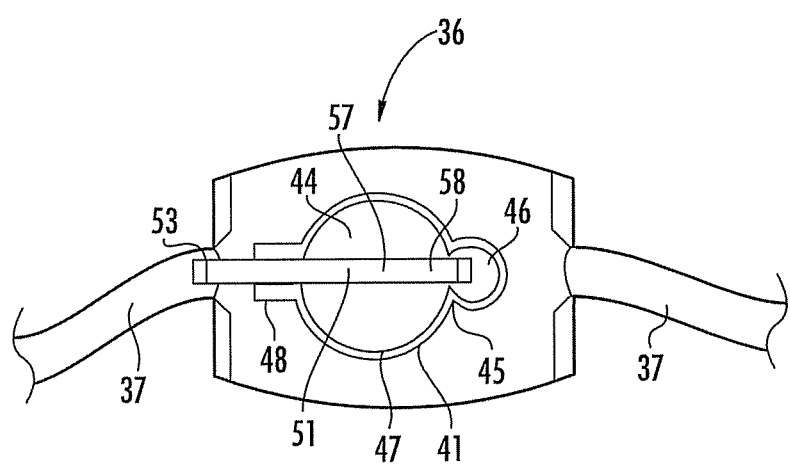
FIG. 4 is top plan view of the ventilation-aid securement device shown in FIG. 1 equipped with the retaining arm.

Referring now to FIGS. 4-6, the retaining arm 51 is used to contact and secure in place the endotracheal tube 14 (see FIGS. 5 and 6). The retaining arm 51 includes an elongated extension portion 57 and a flange 52 (see FIGS. 5 and 6). A first end 58 of the extension portion 57 is formed integral with an end of the flange 52, and the flange 52 extends generally perpendicular to the extension portion 57. The flange 52 includes a hole 59 (see FIG. 5) for receiving the thumbscrew 53. To attach the retaining arm 51 to the ventilation-aid securement device 36, the thumbscrew 53 is inserted through the hole 59 in the flange 52 such that the extension portion 57 extends over the threaded portion 54 of the thumbscrew 53 in a direction opposite a head 55 of the thumbscrew 53. The thumbscrew 53 is then screwed into the threaded opening 49 (see FIG. 5) of the thumbscrew housing 48 such that the extension portion 57 extends over the oxygen-supply inlet aperture 44 of the securement housing 41. Tightening the thumbscrew 53 advances a second opposing end 58 of the extension portion 57 through the narrow opening 45 (see FIG. 4) connecting the oxygen-supply inlet 44 and the tube aperture 46 to contact the endotracheal tube 14. As the second end 58 pushes against the tube 14, the tube 14 is driven against an inside surface of the wall 47 of the securement housing 41. Due to the ovate shape of the tube aperture 46, the tube 14 becomes wedged, thereby further securing the tube 14 in place. An upper surface of the thumbscrew housing 48 contains a recess 50 (see FIG. 1) aligned with the retaining arm 51 to ensure passage of the retaining arm 51 through this portion of the thumbscrew housing 48.

Figure 7:
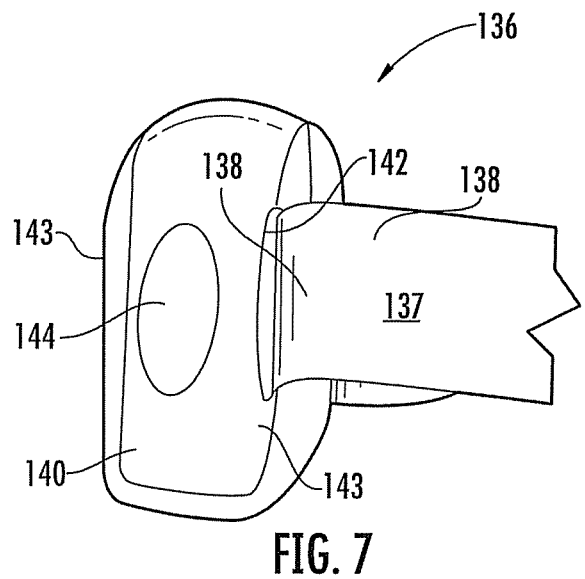
FIG. 7 is a perspective view of a second embodiment of a ventilation-aid securement device, in accord with the present invention.
Figure 8:
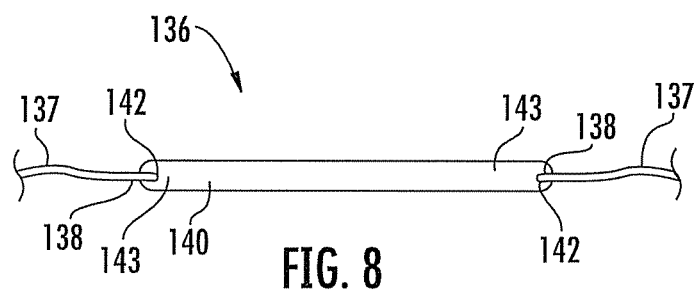
FIG. 8 is a side elevational view of the ventilation-aid securement device shown in FIG. 7.
Figure 9:
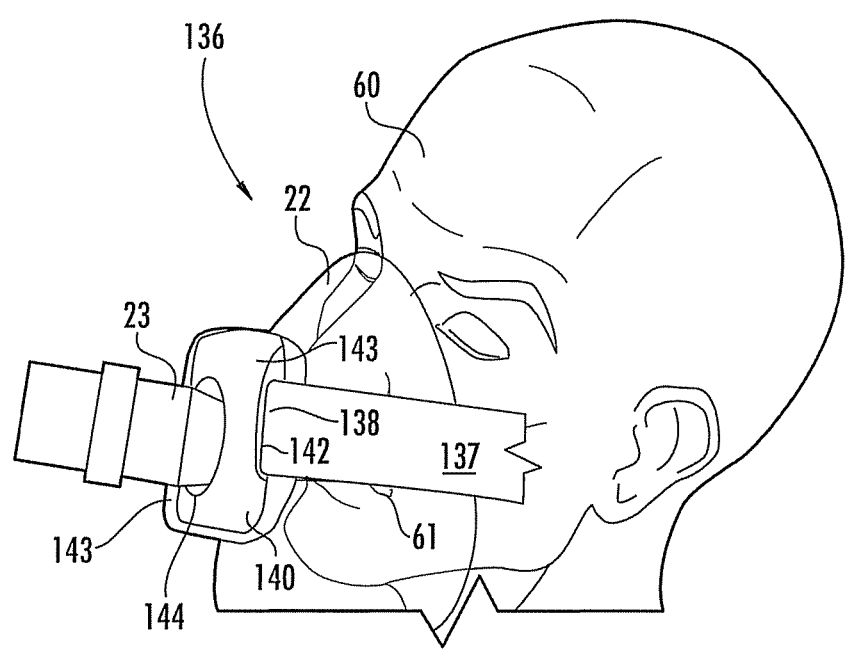
FIG. 9 is a left side perspective view of a patient fitted with a mask secured in place by the ventilation-aid securement device shown in FIG. 7.

FIGS. 7-9 depict a second preferred embodiment of a ventilation-aid securement device 136, in accordance with the present invention. In the present embodiment, the ventilation-aid securement device 136 is configured to secure a mask 22 (see FIG. 9) to a patient 60 (see FIG. 9) using a different configuration than in the first embodiment 36.

Referring now to FIGS. 7-9, the ventilation-aid securement device 136 includes an elongated face plate 140 that is generally rectangular and approximately one-half inch thick. The face plate 140 is flexible so as to conform to a curved surface, such as a surface of a ventilating mask 22 (see FIG. 9). The face plate 140 has opposing side portions 143, each containing a strap opening 142 for receiving an end portion 138 (see FIG. 9) of a strap 137.

Continuing with FIGS. 7-9, the securement device 136 also includes the adjustable strap 137. The strap 137 is placed around the head of the patient 60 and adjustably attached to the securement device 136. A first end portion 138 of the strap 137 is attached to a first strap opening 142 of the face plate 140. A second opposing unattached end portion (not shown) of the strap 137 is equipped with Velcro® permitting the second end portion to be passed through a second strap opening 142 and adjustably secured there. Note that in alternate embodiments, other fastening modes might be used for adjustably securing a strap 137 to a ventilation-aid securement device 136, such as buckles or hook-and-latch systems.

While the invention has been described with respect to certain specific embodiments, it will be appreciated that many modifications and changes may be made by those skilled in the art without departing from the spirit of the invention. It is intended, therefore, that the appended claims cover all such modifications and changes as fall within the true spirit and scope of the invention.

What is claimed as new and what it is desired to secure by Letters Patent of the United States is:

1. A ventilation-aid securement device for securing a ventilating device to a patient comprising:
    a flexible face plate that conforms to a curved surface, the face plate having a centrally-located aperture dimensioned for receiving a ventilating device, and means for adjustably securing the face plate to a patient fitted with the ventilation device such that the ventilation device is properly secured to the patient in a stable position;
    a thumbscrew;
    a securement housing extending from the flexible face plate around the centrally-located aperture of the face plate, the securement housing having a wall defining an oxygen-supply inlet aperture with a first generally cylindrical circumference dimensioned for closely receiving an oxygen-supply inlet of a mask ventilating device and a tube aperture with a second generally cylindrical circumference dimensioned for closely receiving an endotracheal tube of an endotracheal tube ventilating device, a diameter of the oxygen-supply inlet aperture being greater than a diameter of the tube aperture, the first and second circumferences intersecting such that the oxygen-supply inlet aperture and the tube aperture are connected by an opening narrower than the diameters of the oxygen-supply inlet aperture and the tube aperture, the securement housing defining a thumbscrew housing with an opening for receiving the thumbscrew therein, a portion of the thumbscrew being of sufficient length to protrude through the thumbscrew housing to contact and secure in place the oxygen-supply inlet of the mask ventilating device in the oxygen-supply inlet aperture; and
    a retaining arm for contacting and securing in place the endotracheal tube, the retaining arm having an elongated extension portion and a flange, a first end of the extension portion attached to an end of the flange, the flange extending generally perpendicular to the extension portion and having a hole therethrough for receiving the thumbscrew, and an opposing second end of the extension portion for contacting and securing in place the endotracheal tube in the tube aperture, the thumbscrew being of insufficient length to secure the endotracheal tube in the tube aperture without the retaining arm.

2. The ventilation-aid securement device of claim 1, wherein the tube aperture is a generally ovate cylinder.

3. The ventilation-aid securement device of claim 1 wherein the oxygen-supply inlet aperture is positioned between the thumbscrew housing and the tube aperture.

4. The ventilation-aid securement device of claim 3 wherein the opening between the oxygen-supply inlet aperture and the tube aperture is dimensioned for admitting the second end of the extension portion.

5. The ventilation-aid securement device recited in claim 1 wherein the face plate is of sufficient surface area to fit atop a mask of the mask ventilating device in a manner that when secured to the patient provides a seal between the mask and the face of the patient without substantial leakage therebetween.

6. The ventilation-aid securement device recited in claim 5 wherein the adjustably securing means includes a strap of adjustable length for wrapping around the head of the patient having a first end secured to a first side portion of the face plate and an opposing second end detachably secured to an opposing second side portion of the face plate.

7. The ventilation-aid securement device as recited in claim 1, further comprising the mask ventilating device with the oxygen-supply inlet secured in the oxygen-supply inlet aperture by the thumbscrew.

8. The ventilation-aid securement device recited in claim 1, further comprising the endotracheal tube ventilating device with the endotracheal tube secured in the tube opening by the retaining arm.

* * * * *